(12) United States Patent
Krolikowski et al.

(10) Patent No.: US 10,131,569 B2
(45) Date of Patent: Nov. 20, 2018

(54) METHOD FOR THE PREPARATION OF LITHIUM SILICATE GLASSES AND LITHIUM SILICATE GLASS CERAMICS

(71) Applicant: Ivoclar Vivadent AG, Schaan (LI)

(72) Inventors: Sebastian Krolikowski, Lachen (CH); Markus Rampf, Lachen (CH); Christian Ritzberger, Grabs (CH); Harald Bürke, Frastanz (AT); Wolfram Höland, Schaan (LI); Marcel Schweiger, Chur (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/309,819

(22) PCT Filed: May 12, 2015

(86) PCT No.: PCT/EP2015/060457
§ 371 (c)(1),
(2) Date: Nov. 9, 2016

(87) PCT Pub. No.: WO2015/173230
PCT Pub. Date: Nov. 19, 2015

(65) Prior Publication Data
US 2017/0144919 A1    May 25, 2017

(30) Foreign Application Priority Data
May 13, 2014   (EP) .................................... 14168181

(51) Int. Cl.
*C03C 4/12*    (2006.01)
*A61K 6/02*    (2006.01)
(Continued)

(52) U.S. Cl.
CPC .............. *C03C 4/12* (2013.01); *A61K 6/0011* (2013.01); *A61K 6/0094* (2013.01); *A61K 6/025* (2013.01);
(Continued)

(58) Field of Classification Search
CPC ................ C03B 32/02; C03C 10/0027; C03C 10/0045; C03C 10/0054; C03C 10/0009;
(Continued)

(56) References Cited

U.S. PATENT DOCUMENTS 2,284,055 A * 5/1942 Huniger .................... C03C 3/19
252/301.4 R
2,684,911 A * 7/1954 Stookey .................. C03C 3/076
48/31
(Continued)

FOREIGN PATENT DOCUMENTS

CA    2163792 A1   12/1994
CA    2213390 A1   3/1998
(Continued)

OTHER PUBLICATIONS

Buchalla, W., "Comparative Fluorescence Spectroscopy Shows Differences in Noncavitated Enamel Lesions," Caries Research, 2005, 39, pp. 150-156.
(Continued)

*Primary Examiner* — Noah S Wiese
(74) *Attorney, Agent, or Firm* — Ann M. Knab; Thad McMurray

(57) ABSTRACT

The invention relates to a method for the preparation of a lithium silicate glass or a lithium silicate glass ceramic which comprise cerium ions and are suitable in particular for the preparation of dental restorations, the fluorescence properties of which largely correspond to those of natural teeth. The invention also relates to a lithium silicate glass and a lithium silicate glass ceramic which can be obtained using
(Continued)

Figure 1:
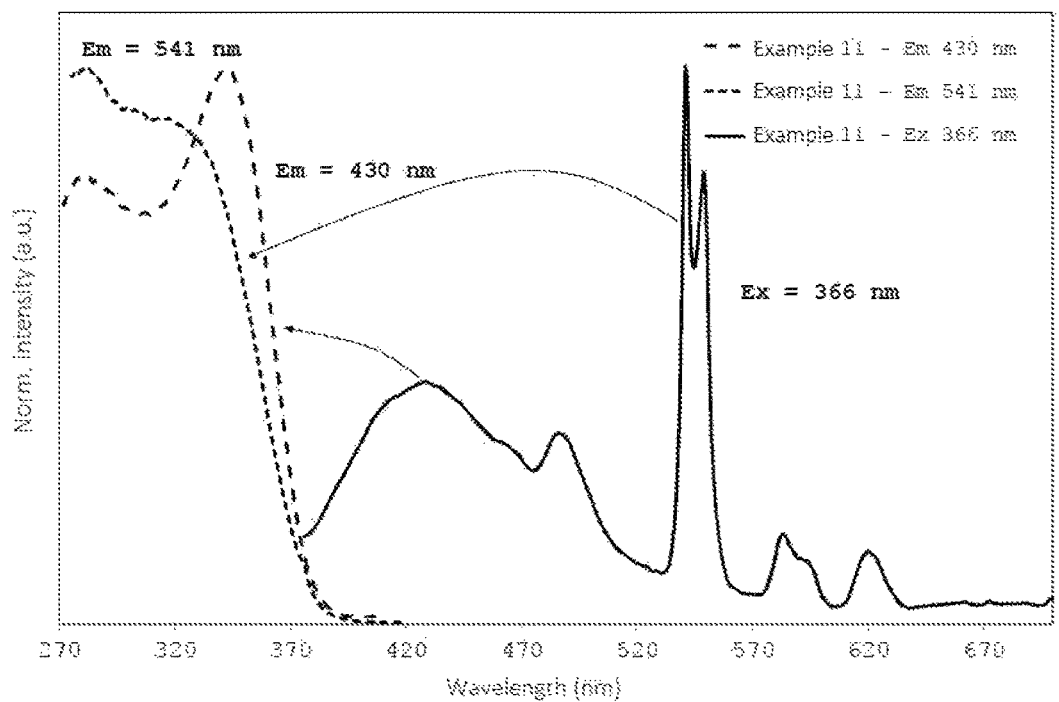

the method according to the invention, the use thereof as dental material and in particular for the preparation of dental restorations, as well as a glass-forming composition which is suitable for use in the method according to the invention.

25 Claims, 2 Drawing Sheets

(51) Int. Cl.
  C03C 3/112 (2006.01)
  C03C 4/00 (2006.01)
  C03C 10/00 (2006.01)
  C09K 11/77 (2006.01)
  A61K 6/00 (2006.01)
  A61K 6/027 (2006.01)
  C03C 1/00 (2006.01)
  C03C 3/097 (2006.01)
  C09K 11/08 (2006.01)
  C03B 5/06 (2006.01)
  C03B 5/193 (2006.01)
  C03B 32/02 (2006.01)

(52) U.S. Cl.
  CPC .......... A61K 6/0205 (2013.01); A61K 6/0215 (2013.01); A61K 6/0235 (2013.01); A61K 6/0273 (2013.01); C03B 5/06 (2013.01); C03B 5/193 (2013.01); C03B 32/02 (2013.01); C03C 1/00 (2013.01); C03C 3/097 (2013.01); C03C 3/112 (2013.01); C03C 4/0021 (2013.01); C03C 10/0009 (2013.01); C03C 10/0027 (2013.01); C09K 11/08 (2013.01); C09K 11/7723 (2013.01); C09K 11/7774 (2013.01); C09K 11/7777 (2013.01); C09K 11/7778 (2013.01); C09K 11/7792 (2013.01); C09K 11/7795 (2013.01); C03C 2204/00 (2013.01)

(58) Field of Classification Search
  CPC ............ A61C 13/0004; A61C 13/0006; A61C 13/083; A61C 8/0012; A61K 6/0273; A61K 6/0094; A61K 6/0215; A61K 6/024
  See application file for complete search history.

(56) References Cited

U.S. PATENT DOCUMENTS

| | | |
|---|---|---|
| 3,006,775 A | 10/1961 | Chen |
| 3,022,180 A | 2/1962 | Morrissey |
| 3,161,528 A | 12/1964 | Eppler |
| 3,252,778 A | 5/1966 | Goodman et al. |
| 3,804,608 A | 4/1974 | Gaskell et al. |
| 3,816,704 A | 6/1974 | Borom et al. |
| 3,977,857 A | 8/1976 | Mattox |
| 4,155,888 A | 5/1979 | Mooth |
| 4,189,325 A | 2/1980 | Barrett et al. |
| 4,414,282 A | 11/1983 | McCollister et al. |
| 4,473,653 A | 9/1984 | Rudoi |
| 4,480,044 A | 10/1984 | McAlinn |
| 4,515,634 A | 5/1985 | Wu et al. |
| 4,671,770 A | 6/1987 | Bell et al. |
| 4,963,707 A | 10/1990 | Zyokou et al. |
| 4,977,114 A | 12/1990 | Horinouchi et al. |
| 5,176,961 A | 1/1993 | Crooker et al. |
| 5,219,799 A | 6/1993 | Beall et al. |
| 5,507,981 A | 4/1996 | Petticrew |
| 5,628,564 A | 5/1997 | Nenyei et al. |
| 5,691,256 A | 11/1997 | Taguchi et al. |
| 5,698,482 A | 12/1997 | Frank et al. |
| 5,702,514 A | 12/1997 | Petticrew |
| 5,707,777 A | 1/1998 | Aoai et al. |
| 5,872,069 A | 2/1999 | Abe |
| 5,874,376 A | 2/1999 | Taguchi et al. |
| 5,938,959 A | 8/1999 | Wang |
| 5,968,856 A | 10/1999 | Schweiger et al. |
| 6,048,589 A * | 4/2000 | Suzuki ................ C03C 10/0027 427/129 |
| 6,066,584 A | 5/2000 | Krell et al. |
| 6,095,682 A | 8/2000 | Hollander et al. |
| 6,106,747 A | 8/2000 | Wohlwend |
| 6,121,175 A | 9/2000 | Drescher et al. |
| 6,157,004 A | 12/2000 | Bizzio |
| 6,163,020 A | 12/2000 | Bartusch et al. |
| 6,174,827 B1 | 1/2001 | Goto et al. |
| 6,252,202 B1 | 6/2001 | Zychek |
| 6,267,595 B1 | 7/2001 | Gratz |
| 6,270,876 B1 * | 8/2001 | Abe .................... C03C 10/0027 428/141 |
| 6,287,121 B1 | 9/2001 | Guiot et al. |
| 6,342,458 B1 | 1/2002 | Schweiger et al. |
| 6,376,397 B1 | 4/2002 | Petticrew |
| 6,420,288 B2 | 7/2002 | Clausbruch et al. |
| 6,441,346 B1 | 8/2002 | Zychek |
| 6,455,451 B1 | 9/2002 | Brodkin et al. |
| 6,485,849 B2 | 11/2002 | Petticrew |
| 6,514,893 B1 | 2/2003 | Schweiger et al. |
| 6,517,623 B1 | 2/2003 | Brodkin et al. |
| 6,593,257 B1 | 7/2003 | Nagata et al. |
| 6,802,894 B2 | 10/2004 | Brodkin et al. |
| 6,818,573 B2 | 11/2004 | Petticrew |
| 7,162,321 B2 | 1/2007 | Luthardt et al. |
| 7,316,740 B2 | 1/2008 | Rheinberger et al. |
| 7,452,836 B2 * | 11/2008 | Apel ....................... C03B 32/02 106/35 |
| 7,655,586 B1 | 2/2010 | Brodkin et al. |
| 7,806,694 B2 | 10/2010 | Brodkin et al. |
| 7,816,291 B2 | 10/2010 | Schweiger et al. |
| 7,867,930 B2 | 1/2011 | Apel et al. |
| 7,867,933 B2 | 1/2011 | Apel et al. |
| 7,871,948 B2 | 1/2011 | Apel et al. |
| 7,892,995 B2 | 2/2011 | Castillo |
| 7,993,137 B2 | 8/2011 | Apel et al. |
| 8,042,358 B2 | 10/2011 | Schweiger et al. |
| 8,047,021 B2 | 11/2011 | Schweiger et al. |
| 8,444,756 B2 | 5/2013 | Schweiger et al. |
| 2001/0006174 A1 | 7/2001 | Brennan |
| 2001/0031446 A1 | 10/2001 | Petticrew |
| 2002/0010063 A1 | 1/2002 | Schweiger et al. |
| 2002/0022563 A1 | 2/2002 | Schweiger et al. |
| 2002/0031670 A1 | 3/2002 | Goto et al. |
| 2002/0035025 A1 | 3/2002 | Schweiger et al. |
| 2002/0160694 A1 | 10/2002 | Wood et al. |
| 2003/0073563 A1 | 4/2003 | Brodkin et al. |
| 2004/0152034 A1 * | 8/2004 | Cummings .......... A61K 6/0276 433/8 |
| 2004/0182538 A1 | 9/2004 | Lambrecht |
| 2005/0098064 A1 | 5/2005 | Schweiger et al. |
| 2005/0127544 A1 | 6/2005 | Brodkin et al. |
| 2006/0082033 A1 | 4/2006 | Hauptmann et al. |
| 2006/0139091 A1 | 6/2006 | Fratti |
| 2006/0257823 A1 | 11/2006 | Pfeiffer et al. |
| 2006/0257824 A1 | 11/2006 | Pfeiffer et al. |
| 2007/0023971 A1 | 2/2007 | Saha et al. |
| 2008/0120994 A1 | 5/2008 | Schweiger et al. |
| 2008/0199823 A1 | 8/2008 | Miller |
| 2009/0023574 A1 | 1/2009 | Holand et al. |
| 2009/0038344 A1 | 2/2009 | Apel et al. |
| 2009/0038508 A1 | 2/2009 | Apel et al. |
| 2009/0042166 A1 | 2/2009 | Craig et al. |
| 2009/0256274 A1 | 10/2009 | Castillo |
| 2009/0258778 A1 | 10/2009 | Castillo |
| 2010/0083706 A1 | 4/2010 | Castillo |
| 2011/0256409 A1 | 10/2011 | Ritzberger et al. |
| 2012/0094822 A1 | 4/2012 | Castillo et al. |
| 2012/0148988 A1 | 6/2012 | Castillo et al. |
| 2012/0212962 A1 * | 8/2012 | Yasumori ................ C03C 3/089 362/260 |
| 2012/0248642 A1 | 10/2012 | Ritzberger et al. |

(56) References Cited

U.S. PATENT DOCUMENTS

2012/0309607 A1  12/2012  Durschang et al.
2014/0141960 A1  5/2014   Borczuch-Laczka et al.

FOREIGN PATENT DOCUMENTS

| CA | 2252660 A1 | 5/1999 |
|---|---|---|
| DE | 2451121 A1 | 5/1975 |
| DE | 4303458 C1 | 1/1994 |
| EP | 1152641 A2 | 11/2001 |
| EP | 1505041 A1 | 2/2005 |
| EP | 1688398 A1 | 8/2006 |
| GB | 752243 A | 7/1956 |
| GB | 2284655 A | 6/1995 |
| JP | H10323354 A | 12/1998 |
| JP | 11-74418 A | 3/1999 |
| JP | 2005-062832 A | 3/2005 |
| WO | 2007028787 A1 | 3/2007 |

OTHER PUBLICATIONS

Rukmani, S.J. et al., "Effects of V and Mn Colorants on the Crystallization Behavior and Optical Properties of Ce-Doped Li-Disilicate Glass-Ceramics," J. Am. Ceram. Soc., 2007, 90, pp. 706-711.

Bei, J. et al., "Optical Properties of Ce3+-Doped Oxide Glasses and Correlations with Optical Basicity," Materials Research Bulletin, Elsevier, 2007, 42(7), pp. 1195-1200.

Apel, E. et al., "Influence of ZrO2 on the crystallization and properties of lithium disilicate glass-ceramics derived from multi-component system", Journal of European Ceramic Society, 2007, 27, 1571-1577.

Durschang, Dr. Bernhard, "Report of Results", Fraunhofer Institute for Silicate Research ISC Glass and Mineral Materials, 2015.

McMillan, P.W. et al., "The Structure and Properties of a Lithium Zinc Silicate Glass-Ceramic", Journal of Material Science 1966, I. 269-279.

Deubener, J. et al., "Induction time analysis of nucleation and crystal grown in di- and metasilicate glasses", Journal of Non-Crystalline Solids 1993, 163, 1-12.

Holand, W. et al., "Glass-ceramic technology", American Chemical Society 2002, Westerville OH, USA.

Holand, W., et al., "Control of nucleation in glass ceramics", Phil. Trans. Soc. Lond. A 2003, 361, 575-589.

Holand, W. et al., "Principles and phenomena of bioengineering with glass-ceramics of dental restoration", Journal of the European Ceramics Society 2007, 27, 1571-1577.

Ivoclar Vivadent, Inc., IPS e.max lithium disilicate, 627329, Rev. Feb. 2009.

Borom, M.P., et al., "Strength and Microstructure in Lithium Disilicate Glass Ceramics", J. Am. Ceram. Soc., 1975,58, 385-391.

Von Clausbruch, et al., "Effect of ZnO on the Crystallization, Microstructure, and Properties of Glass-Ceramics in the SiO2—Li2O—K2O—P2O5 System," Glastech. Ber. Glass Sci. Technol. 74(8):223-229(2001).

Von Clausbruch, et al., "Effect of P2O5 on the Crystallization and Microstructure of Glass-Ceramics in the SiO2—Li2O—Zn)—P2O5 System," Glastech. Ber. Glass Sci. Technol. 74(8):223-229(2001).

Stookey, S.D. "Chemical Machining of Photosensitive Glass," Ind. Eng. Chem. 45:115-118 (1993).

Oliveria et al., "Sintering and Crystallization of a GlassPowder in the Li2O—ZrO2—SiO2 System," J. Amer. Ceramic Soc. 81(3):777-780 (1998).

Montedo, et al., "Low Thermal Expansion Sintered LZSA Glass-Ceramics," American Ceramic Society Bulletin, vol. 87, No. 7, pp. 34-40.

Giassi, et al., "Injection Moulding of LiO2—ZrO2—SiO2—Al2O3 (LZSA) Glass Ceramics," Glass Technol., 46(3), 277-280 (2005).

http://en.wikipedia.org/wiki/Nucleation ; Sep. 20, 2012.

International Preliminary Report on Patentability of PCT/EP2015/060457, dated Nov. 15, 2016, 10 pages.

\* cited by examiner

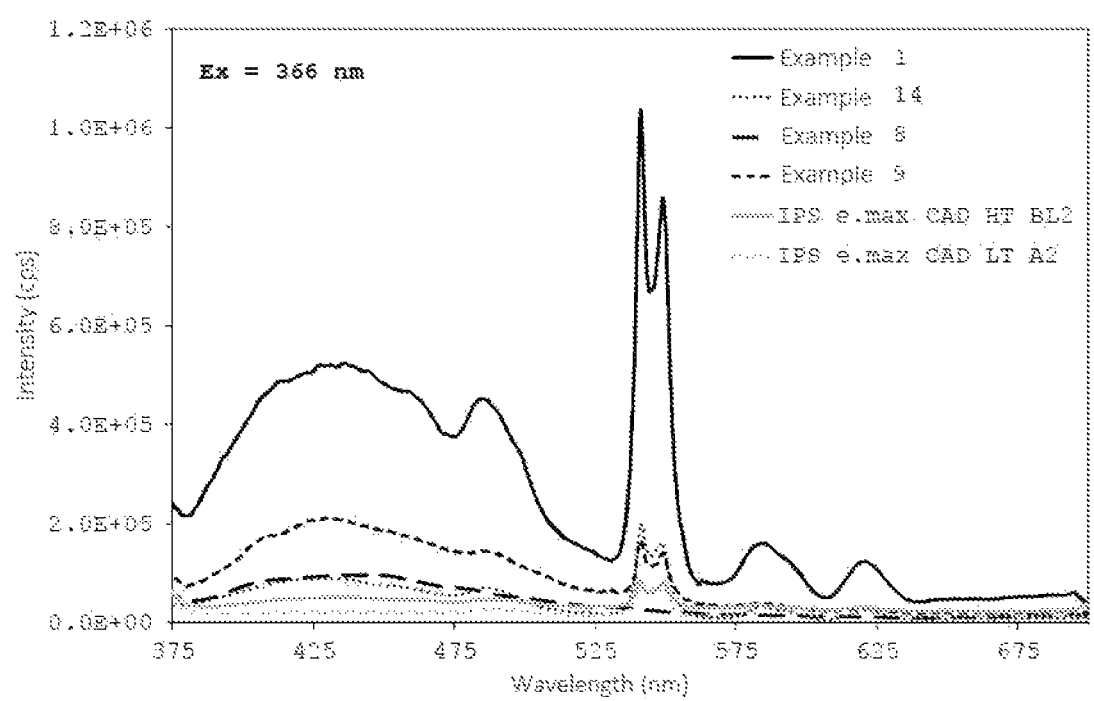

METHOD FOR THE PREPARATION OF LITHIUM SILICATE GLASSES AND LITHIUM SILICATE GLASS CERAMICS

CROSS-REFERENCE TO RELATED APPLICATIONS

This application is a National Stage application of International patent application PCT/EP2015/060457 filed on May 12, 2015, which claims priority to European patent application No. 14168181.7 filed on May 13, 2014, the disclosures of which are incorporated herein by reference in their entirety.

The present invention relates to a method for the preparation of a lithium silicate glass or a lithium silicate glass ceramic which contain cerium ions and are suitable in particular for the preparation of dental restorations, the fluorescence properties of which largely correspond to those of natural teeth. The invention also relates to a lithium silicate glass and a lithium silicate glass ceramic which can be obtained using the method according to the invention, the use thereof as dental material and in particular for the preparation of dental restorations, as well as a glass-forming composition which is suitable for use in the method according to the invention.

Lithium silicate glass ceramics are used in dentistry, in particular for the preparation of dental crowns and small bridges, because of their high translucence and very good mechanical properties. The known lithium silicate glass ceramics usually contain $SiO_2$, $Li_2O$, $Al_2O_3$, $Na_2O$ or $K_2O$ and nucleating agent such as $P_2O_5$ as main components.

EP 0 916 625 A1 describes translucent lithium disilicate glass ceramic products which can be prepared as blanks and can be processed, in particular by plastic deformation under the action of pressure and heat or machining, to form shaped translucent dental products with high strength. To prepare the lithium disilicate glass ceramic products, firstly a melt of a starting glass is produced which contains the components $SiO_2$, $Li_2O$, $La_2O_3$ and/or $Al_2O_3$ and MgO and/or ZnO. This melt is shaped and cooled in a suitable manner and subjected to at least one heat treatment in order to obtain a glass ceramic product in the form of a blank. In order to match the colour of the glass ceramic products to the colour of natural tooth material, the starting glass can furthermore have colour and fluorescence components which are preferably selected from the group consisting of $CeO_2$, $V_2O_5$, $Fe_2O_3$, $MnO_2$, $TiO_2$, $Y_2O_3$, $Er_2O_3$, $Tb_4O_7$, $Eu_2O_3$, $Yb_2O_3$, $Gd_2O_3$, $Nd_2O_3$, $Pr_2O_3$, $Dy_2O_3$, $Ag_2O$, $SnO_2$ and $Ta_2O_5$.

EP 1 505 041 A1 describes lithium metasilicate glass ceramics which are processed, in particular by means of CAD/CAM methods, to form dental restorations and can be converted into high-strength lithium disilicate glass ceramics by a subsequent heat treatment. To prepare the glass ceramics, firstly a melt of a starting glass is formed which contains $SiO_2$, $Li_2O$, $Al_2O_3$, $K_2O$ and a nucleating agent such as $P_2O_5$ as main components. The melt of the starting glass is shaped and cooled in a suitable manner and subjected to two heat treatments in order to obtain a glass ceramic product in the form of a blank. The starting glass can have, among other things, colouring and fluorescent metal oxides. The metal is preferably selected from the group consisting of Ta, Tb, Y, La, Er, Pr, Ce, Ti, V, Fe and Mn, wherein in the examples the oxides $TiO_2$, $V_2O_5$, $Fe_2O_3$, $MnO_2$, $CeO_2$, $Y_2O_3$, $La_2O_3$, $Pr_2O_3$, $Ta_2O_5$, $Tb_4O_7$ and $Er_2O_3$ are used. Similar lithium silicate glass ceramics are described in EP 1 688 398 A1.

From W. Buchalla, "Comparative Fluorescence Spectroscopy Shows Differences in Non-Cavitated Enamel Lesions", Caries Res. 2005, 39, 150-156, it is known that natural teeth display a bluish-white fluorescence with wavelengths in the range of from 400 to 650 nm under ultraviolet light.

Rukmani et al., J. Am. Ceram. Soc. 2007, 90, 706-711, describe the influence of V and Mn colorants on the crystallization behaviour and the optical properties of Ce-doped lithium disilicate glass ceramics. To prepare the glass ceramics, a mixture of the starting materials $SiO_2$, $ZrO_2$, $Li_2CO_3$, $K_2CO_3$, $MgCO_3$ and $Al(PO_3)_3$ is mixed with $CeO_2$, $V_2O_5$ and $MnO_2$, the mixture is melted at 1500° C. in platinum crucibles, cooled and then subjected to several heat treatments in a tube furnace with air supply.

However, it has been shown that the lithium silicate glass ceramics known from the state of the art have insufficient fluorescence properties and cannot imitate the fluorescence properties of natural tooth material to a sufficient extent, in particular under UV light. Dental restorations prepared from such glass ceramics thereby become recognizable as restorations, in particular under the influence of UV light, or are perceived as tooth gaps or defects.

Starting from the above-described disadvantages of the already known glass ceramics, the object of the invention is to provide a glass ceramic which displays a fluorescence comparable to natural tooth material and is suitable for the preparation of dental restorations which can largely imitate the colour and fluorescence properties of natural tooth material, in particular even under UV light.

This object is achieved according to the invention by a method for the preparation of a lithium silicate glass or a lithium silicate glass ceramic which comprises a step in which a melt of a starting glass which contains cerium ions is exposed to reducing conditions.

It has surprisingly been shown that the method according to the invention makes it possible to prepare lithium silicate glasses and lithium silicate glass ceramics which display fluorescence properties that are improved compared with the state of the art, in particular under the action of UV light.

Without being limited to a particular theory, it is assumed that an equilibrium between $Ce^{3+}$ ions and $Ce^{4+}$ ions is established in glass melts which contain cerium ions. It is further assumed that the reducing conditions to which the starting glass is exposed in the method according to the invention shift this ratio in favour of $Ce^{3+}$ ions, which display a fluorescence in the wavelength range of from 320 to 500 nm because of 5d→4f transitions. This fluorescence is particularly suitable for imitating the fluorescence properties of natural tooth material.

Usually the method according to the invention includes reacting the melt of the starting glass with at least one reducing agent. In principle, all agents which are capable of reducing $Ce^{4+}$ ions to $Ce^{3+}$ ions under the conditions of the method according to the invention come into consideration as reducing agents. Those reducing agents which can be removed from the glass melt without leaving a residue after the reduction are preferred.

In particular gaseous reducing agents, as well as reducing agents which, under the conditions of the method according to the invention, are burnt out of the glass melt after the reduction, are preferred. Examples of gaseous reducing agents are gases which contain hydrogen and preferably mixtures of hydrogen and nitrogen.

Examples of reducing agents are furthermore substances which contain at least one oxidizable carbon atom, in particular carbon, for example graphite, organic salts, carbohydrates and cereal flours.

According to a preferred embodiment the melt of the starting glass is formed from a glass-forming composition which contains $SiO_2$, $Li_2O$, nucleating agent, a cerium compound and at least one reducing agent. A compound which contains at least one oxidizable carbon atom and is preferably selected from the group consisting of organic salts, carbohydrates and cereal flours is preferred as the at least one reducing agent. Examples of particularly suitable organic salts are acetylacetonates.

In a particularly preferred embodiment a cerium acetylacetonate, in particular cerium(III) acetylacetonate, is used as reducing agent. According to this embodiment the cerium compound represents at the same time the at least one reducing agent.

According to a further preferred embodiment the at least one reducing agent is a reducing gas, wherein the gas preferably contains hydrogen and preferably contains hydrogen and nitrogen. Mixtures of hydrogen and nitrogen which contain about 5 vol.-% hydrogen and are also called forming gas are particularly suitable. The extent of the reduction can be controlled via the quantity of the gas supplied and in particular via the flow rate and duration of the supply of the gas. The quantity of the active component of the reducing gas, preferably hydrogen, is preferably 0.05 to 5 l/min, in particular 0.1 to 1 l/min and preferably 0.2 to 0.5 l/min, for a duration of from 10 to 180 min, in particular 20 to 120 min and preferably 30 to 90 min.

It is preferred according to the invention that the starting glass contains 0.1 to 7.0 wt.-%, in particular 0.5 to 5.0 wt.-% and preferably 1.0 to 4.0 wt.-% cerium ions, calculated as $CeO_2$.

According to a particularly preferred embodiment the melt of the starting glass is formed from a glass-forming composition which contains at least one cerium(III) compound and at least one cerium(IV) compound. The ratio of $Ce^{3+}$ ions and $Ce^{4+}$ ions in the obtained lithium silicate glass or the lithium silicate glass ceramic can additionally be adjusted by varying the ratio of cerium(III) compound to cerium(IV) compound. In addition, $Ce^{4+}$ ions bring about a yellowing of the lithium silicate material. Thus a particularly good imitation of the fluorescence and colour properties of natural tooth material is made possible. In a particularly preferred embodiment the glass-forming composition contains 0.1 to 5.0 wt.-%, in particular 0.5 to 3.0 and preferably 1.5 to 2.0 wt.-% cerium(III) compound, calculated as $Ce_2O_3$, and 0.1 to 5.0 wt.-%, in particular 0.5 to 3.0 and preferably 1.5 to 2.0 wt.-% cerium(IV) compound, calculated as $CeO_2$. It is further preferred that the mass ratio of cerium(III) compound, calculated as $Ce_2O_3$, to cerium(IV) compound, calculated as $CeO_2$, lies in the range of from 5:1 to 1:5, in particular 2:1 to 1:2 and preferably 1.25:1 to 1:1.25.

The starting glass furthermore contains at least the components, $SiO_2$, $Li_2O$ and nucleating agent, necessary for forming a lithium silicate crystal phase.

The starting glass preferably contains 55.0 to 75.0 wt.-%, in particular 59.0 to 73.0 wt.-%, preferably 60.0 to 71.0 wt.-% and particularly preferably 60 to 69 wt.-% $SiO_2$.

Moreover, a starting glass is preferred which contains 9.0 to 21.0 wt.-%, in particular 13.0 to 19.0 wt.-% and preferably 11.0 to 15.0 wt.-% $Li_2O$.

Furthermore, it has proved particularly preferable if the starting glass contains 0.5 to 12.0 wt.-% and in particular 2.5 to 7.0 wt.-% nucleating agent. Preferred nucleating agents are $P_2O_5$, $TiO_2$, $Nb_2O_5$, metals, e.g. Pt, Pd, Au and Ag, and mixtures thereof. The starting glass particularly preferably contains $P_2O_5$ as nucleating agent.

The starting glass preferably contains further alkali metal oxide in an amount of from 1.0 to 10.0 wt.-%, in particular 1.0 to 10.0 wt.-%, preferably 2.0 to 7.0 wt.-% and particularly preferably 2.0 to 5.0 wt.-%. The term "further alkali metal oxide" refers to alkali metal oxide with the exception of $Li_2O$. The further alkali metal oxide is in particular $Na_2O$, $K_2O$, $Cs_2O$ and/or $Rb_2O$ and is particularly preferably $K_2O$. It is preferred that the starting glass contains less than 2.0 wt.-%, in particular less than 1.0 wt.-%, preferably less than 0.5 wt.-% and particularly preferably essentially no $Na_2O$.

It is further preferred that the starting glass contains up to 5.0 wt.-% alkaline earth metal oxide, wherein the alkaline earth metal oxide is in particular CaO, BaO, MgO, SrO or a mixture thereof.

A starting glass which contains 0.5 to 5.0, in particular 2.5 to 7.0 and preferably 2.5 to 3.5 wt.-% oxide of trivalent elements is further preferred, wherein this oxide is selected in particular from $Al_2O_3$, $Y_2O_3$, $La_2O_3$, $Bi_2O_3$ and mixtures thereof, and preferably is $Al_2O_3$.

A starting glass which contains at least one and preferably all of the following components is particularly preferred:

| Component | wt.-% |
|---|---|
| $SiO_2$ | 55.0 to 75.0, in particular 59.0 to 73.0 |
| $Li_2O$ | 9.0 to 21.0, in particular 13.0 to 19.0 |
| $M_2O$ | 1.0 to 12.0, in particular 2.0 to 5.0 |
| $Al_2O_3$ | 0.5 to 5.0, in particular 2.5 to 3.5 |
| $P_2O_5$ | 0.5 to 12.0, in particular 2.5 to 7.0, | wherein $M_2O$ is selected from the group consisting of $Na_2O$, $K_2O$, $Rb_2O$ and $Cs_2O$, and preferably is $K_2O$.

The starting glass can moreover also contain additional components which are selected in particular from oxides of tetravalent elements, further oxides of pentavalent elements, oxides of hexavalent elements, melt accelerators, as well as further colorants and fluorescent agents.

The term "further oxides of tetravalent elements" refers to oxides of tetravalent elements with the exception of $SiO_2$. Examples of further oxides of tetravalent elements are $ZrO_2$, $SnO_2$ and $GeO_2$. In a preferred embodiment the starting glass contains 0.1 to 15 wt.-%, in particular 1 to 10 wt.-%, preferably 2 to 8 wt.-% and most preferably 4 to 6 wt.-% $ZrO_2$.

The term "further oxides of pentavalent elements" refers to oxides of pentavalent elements with the exception of $P_2O_5$. An example of a further oxide of pentavalent elements is $Bi_2O_5$.

Examples of oxides of hexavalent elements are $WO_3$ and $MoO_3$.

A glass ceramic is preferred which contains at least one further oxide of tetravalent elements, one further oxide of pentavalent elements or one oxide of hexavalent elements.

Examples of melt accelerators are fluorides.

Examples of further colorants and fluorescent agents are oxides of d- and f-elements, such as the oxides of Sc, Ti, V, Mn, Fe, Ag, Ta, W, Pr, Nd, Eu, Gd, Tb, Dy, Er, Tm and Yb and in particular of V, Mn, Eu, Dy, Er and Tm.

In a particular embodiment the starting glass furthermore contains terbium ions. The starting glass preferably contains 0.05 to 2.0, in particular 0.1 to 1.5, preferably 0.2 to 1.0 and particularly preferably 0.3 to 0.7 wt.-% terbium ions, calculated as $Tb_4O_7$. It has surprisingly been shown that according to the invention it is possible, by combining cerium ions and terbium ions, to obtain lithium silicate glasses and lithium silicate glass ceramics, the fluorescence and colour properties of which can imitate those of natural tooth material particularly well. It is particularly surprising that in the case of the glasses and glass ceramics prepared according to the invention the fluorescence brought about by the cerium ions largely persists even in the presence of terbium ions, although a reduction or even complete disappearance of the fluorescence brought about by cerium ions in the presence of d-elements was observed in the state of the art.

The melt of the starting glass is preferably formed at temperatures of in particular from 1300 to 1600° C. The procedure is in particular that a mixture of suitable starting materials, such as carbonates, oxides, phosphates and fluorides, is melted at temperatures of from 1300 to 1600° C. for 2 to 10 h. Where a gas is used as reducing agent, the gas is passed through the thus-obtained glass melt. To achieve a particularly high homogeneity, the obtained glass melt can then be poured into water in order to form a glass granulate, and the obtained granulate can then be melted again.

The melt can then be poured into moulds to produce blanks of the starting glass, so-called solid glass blanks or monolithic blanks. It is also possible to put the melt into water again in order to prepare a granulate. This granulate can then be pressed, after grinding and optionally addition of further components, to form a blank, a so-called powder compact. Finally, the starting glass can also be processed to form a powder after granulation.

The starting glass, e.g. in the form of a solid glass blank, a powder compact or in the form of a powder, can then be subjected to at least one heat treatment in the range of from 450 to 950° C. It is preferred that firstly a first heat treatment is carried out at a temperature in the range of from 500 to 600° C. to prepare a glass with nuclei which are suitable for forming lithium metasilicate and/or lithium disilicate crystals. This glass can then preferably be subjected to at least one further temperature treatment at a higher temperature and in particular more than 570° C. to effect crystallization of lithium metasilicate or lithium disilicate.

The term "main crystal phase" used in the following refers to the crystal phase which has the highest proportion by volume compared with other crystal phases.

The glass ceramic obtained using the method according to the invention preferably has lithium metasilicate as main crystal phase. In an embodiment the glass ceramic contains more than 10 vol.-%, preferably more than 20 vol.-% and particularly preferably more than 30 vol.-% lithium metasilicate crystals, relative to the total glass ceramic.

In a further preferred embodiment, the glass ceramic has lithium disilicate as main crystal phase. In an embodiment the glass ceramic contains more than 10 vol.-%, preferably more than 20 vol.-% and particularly preferably more than 30 vol.-% lithium disilicate crystals, relative to the total glass ceramic.

The invention furthermore relates to a lithium silicate glass, a lithium silicate glass with nuclei suitable for forming lithium metasilicate and/or lithium disilicate crystals and a lithium silicate glass ceramic, which can be obtained using the method according to the invention. Preferred embodiments for the lithium silicate glass, the lithium silicate glass with nuclei suitable for forming lithium metasilicate and/or lithium disilicate crystals and the lithium silicate glass ceramic result from the preferred embodiments described above for the method according to the invention.

The invention furthermore relates to a lithium silicate glass, a lithium silicate glass with nuclei suitable for forming lithium metasilicate and/or lithium disilicate crystals and a lithium silicate glass ceramic, which have a fluorescence intensity at 430 nm and/or in the wavelength range of from 400 to 460 nm (area under the curve) which is at least 1.5 times, in particular at least 2 times, preferably at least 4 times, particularly preferably at least 6 times, the corresponding fluorescence intensity of a reference sample, wherein the reference sample can be obtained by melting a starting glass with the composition: 71.3 wt.-% $SiO_2$, 15.1 wt.-% $Li_2O$, 3.2 wt.-% $K_2O$, 3.5 wt.-% $Al_2O_3$, 3.3 wt.-% $P_2O_5$, 1.5 wt.-% $CeO_2$ and 0.7 wt.-% $Tb_4O_7$ on a scale of 200 g from suitable raw materials in a platinum-rhodium crucible at 1500° C. for 1 h, pouring 30 g of the glass melt into a pre-heated mould to produce a glass block, and converting the glass block into a glass ceramic by successive temperature treatments at 500° C. for 10 min, 700° C. for 20 min and 850° C. for 10 min, wherein the heating rates between the temperature treatments are 30 K/min in each case.

Preferably, the lithium silicate glass and the lithium silicate glass ceramic furthermore have a fluorescence intensity at 541 nm and/or in the wavelength range of from 535 to 555 nm (area under the curve) which is at least 1.5 times, in particular at least 2 times, preferably at least 3 times, particularly preferably at least 4 times, the corresponding fluorescence intensity of a reference sample, wherein the reference sample can be obtained as described above.

Lithium silicate glasses and lithium silicate glass ceramics are particularly preferred which have a fluorescence intensity in the wavelength range of from 375 to 700 nm (area under the curve) which is at least 1.5 times, in particular at least 2 times, preferably at least 3 times, particularly preferably at least 4 times, the corresponding fluorescence intensity of a reference sample, wherein the reference sample can be obtained as described above.

The fluorescence is typically measured using platelets with the dimensions: 17.9 mm×15.9 mm×2 mm, the surface of which has been polished with an APEX grinding wheel (0.5 μm), by means of a fluorescence spectrometer of the FL1039 type (Horiba Jobin Yvon GmbH) with a 450 W xenon lamp, an excitation monochromator (gap width 1 nm, excitation wavelength 366 nm), an emission monochromator (gap width 1.5 nm, scan range 372 to 700 nm, increment 1 nm) and a photomultiplier detector (integration time 1 s) of the PMT 1424M type (Horiba Jobin Yvon GmbH). The platelet is typically placed at an angle of 30° relative to the excitation monochromator and the emission is measured at an angle of 90° relative to the excitation monochromator with an optical 5% Neutral Density Filter.

The invention furthermore relates to a lithium silicate glass, a lithium silicate glass with nuclei suitable for forming lithium metasilicate and/or lithium disilicate crystals and a lithium silicate glass ceramic, which have a whitish/blue fluorescence colour in the CIE colour space.

Dental restorations, such as inlays, onlays, veneers, partial crowns, crowns, facets or abutments, can be prepared from the lithium silicate glass according to the invention, the lithium silicate glass according to the invention with nuclei suitable for forming lithium metasilicate and/or lithium disilicate crystals and the lithium silicate glass ceramic according to the invention. The invention therefore also relates to their use as dental material and in particular for the preparation of dental restorations.

It is preferred that the glass ceramic or the glass is shaped to form the desired dental restoration by pressing or machining. The pressing is usually carried out under increased pressure and at increased temperature. Above all, the lithium silicate glass according to the invention and in particular the lithium silicate glass with nuclei according to the invention, the lithium metasilicate glass ceramic according to the invention and the lithium disilicate glass ceramic according to the invention can be used in a suitable manner, e.g. in the form of blanks, for the pressing. The machining is usually carried out during a CAD/CAM method, and in particular it uses the lithium metasilicate and lithium disilicate glass ceramic according to the invention, preferably in the form of suitable blanks. After the preparation by pressing or machining of the dental restoration shaped as desired, it can in particular still be heat-treated in order to convert precursors used, such as lithium silicate glass, lithium silicate glass with nuclei or lithium metasilicate glass ceramic, into lithium disilicate glass ceramic.

Finally, the invention also relates to a glass-forming composition which contains $SiO_2$, $Li_2O$, nucleating agent, a cerium compound and at least one reducing agent. This composition is particularly suitable for use in the above-described method according to the invention. Preferred embodiments of the glass-forming composition result from the preferred embodiments described above for the method according to the invention.

The invention is explained in more detail below by means of embodiment examples.

EXAMPLES

A total of 16 glasses and glass ceramics with the compositions given in Table I were prepared by melting corresponding starting glasses, followed by heat treatment according to Table II for controlled nucleation and crystallization, wherein in Table I the oxidation states of the given oxides refer to the oxidation states of the raw materials used for melting the starting glasses. The following meanings apply in Table II $T_N$ and $t_N$ temperature and time used for nucleation
$T_{k1}$ and $t_{k1}$ temperature and time used for first crystallization
$T_{K2}$ and $t_{K2}$ temperature and time used for second crystallization.

Examples 1 to 10: Use of a Reducing Cerium Compound as Reducing Agent

To prepare glasses and glass ceramics using a cerium compound as reducing agent, firstly starting glasses corresponding to the compositions given in Table I on a scale of 100 to 200 g were melted from a mixture of usual raw materials at 1500° C. for 2 h in a platinum crucible, wherein cerium(III) acetylacetonate was used as raw material for the given $Ce_2O_3$ content. By pouring the starting glasses into water, glass frits were prepared which were dried in a drying furnace at 150° C. and then melted a second time at 1500° C. for 2.5 h for homogenization. The obtained glass melts were then poured into pre-heated moulds to produce glass blocks.

The glass blocks were then converted to glasses and glass ceramics by thermal treatment. The thermal treatments used for controlled nucleation and controlled crystallization are given in Table II.

Examples 11 to 15: Use of Forming Gas as Reducing Agent

To prepare glasses and glass ceramics using forming gas as reducing agent, firstly starting glasses corresponding to the compositions given in Table I on a scale of 200 g were melted from usual raw materials in a platinum-rhodium crucible at 1450 to 1500° C. for 1 h. Then, 30 g of the glass melts, as reference samples, were poured into pre-heated moulds in order to produce glass blocks. About 3 l/min forming gas (95% $N_2$, 5% $H_2$) was passed through the remaining glass melt for 30 to 90 min by means of a quartz glass dip tube. The dip tube was then removed from the melt and the melt surface was flushed with forming gas for about 30 min in order to prevent a reoxidation. The glass melt was then poured into pre-heated moulds to produce glass blocks. The subsequent temperature treatments (nucleation, crystallization and/or pressing) were carried out in a normal furnace atmosphere.

No effects of the melting under forming gas on the crystallization and/or crystalline structure were observed.

Example 16: Use of an Organic Compound as Reducing Agent

To prepare glasses and glass ceramics using an organic compound as reducing agent, a starting glass corresponding to the composition given in Table I for Example 11 on a scale of 200 g was melted from a mixture of usual raw materials, accompanied by the addition of 1.5 wt.-% saccharose in a platinum crucible by heating to 1450° C. at a heating rate of 10 K/min. After a holding time of 30 min, the obtained glass melt was fritted in water and then dried. The frit was melted again at 1500° C. for 1 h and poured into a graphite mould in order to produce glass blocks.

The glass blocks were then converted to glasses and glass ceramics by thermal treatment. For this, the glass blocks were tempered immediately after the casting and demoulding in a muffle furnace at 490° C. for 10 min and then cooled slowly to room temperature.

A disc about 2 mm thick was sawn off from the glass block and then crystallized in a Programat furnace (Ivoclar Vivadent AG) via a temperature treatment at 840° C. for 7 min. The thus-obtained white lithium disilicate glass ceramic displayed a strong white-bluish fluorescence under excitation by UV light.

The fluorescence of this sample is strongly increased compared with a conventionally melted glass ceramic and lies in the range of the sample which was prepared by means of passing forming gas through it.

Determination of Biaxial Strengths

With the aid of a Sirona grinding unit, platelets with thicknesses of about 2 mm were ground out of the blocks obtained after nucleation and first crystallization via the CAD/CAM method. The platelets were then subjected to a further temperature treatment according to Table II in a Programat furnace (Ivoclar Vivadent AG) for the second crystallization. In a further processing step, the platelets were ground to a thickness of about 1.3 mm and the surface was polished with a diamond grinding wheel (15 μm). The average biaxial strengths determined using the thus-obtained samples are given in Table II.

Determination of Colour Values

Discs about 2.5 mm thick were sawn off from the blocks obtained after nucleation and first crystallization and subjected to a further temperature treatment according to Table II for the second crystallization. For the determination of the colour values, the platelets were ground to a thickness of 2 mm with a 1000 grit SiC sandpaper. The measured colour values were measured in the measurement range of 400-700 nm by means of a CM-3700d spectrophotometer (Konica-Minolta). The colour values were determined according to DIN5033 and DIN6174 and the CR value according to British Standard BS56129.

Fluorescence Measurements

With the aid of a Sirona grinding unit, platelets were ground out of the blocks obtained after nucleation and first crystallization via the CAD/CAM method. The platelets were then subjected to a further temperature treatment according to Table II in a Programat furnace (Ivoclar Vivadent AG) for the second crystallization. In a further processing step, the platelets were ground to the dimensions 17.9 mm×15.9 mm×2 mm and the surface was polished with an APEX grinding wheel (0.5 μm).

To measure the fluorescence properties, a fluorescence spectrometer of the FL1039 type (Horiba Jobin Yvon GmbH) with an excitation monochromator and an emission monochromator was used. The excitation of the samples was carried out by means of a 450 W xenon lamp. The emission intensity was determined using a photomultiplier detector (PMT) of the PMT 1424M type (Horiba Jobin Yvon GmbH) as pulses per second (counts per second, cps). The calibration of the excitation monochromator was carried out by means of an integrated silicon photodiode. The emission monochromator was calibrated via the position of the water Raman peak. The linearity of the detector in the measurement range was ensured via device-specific correction data sets. The linearity of the excitation intensity was ensured during the determination of the excitation spectra via a mathematical correction of the measured emission intensity via the lamp intensity (division of the measured signal by the reference signal of the integrated silicon photodiode which directly determines the lamp intensity). To protect the detector and in order not to reach the saturation range, a 5% Neutral Density Filter was used in the emission beam path.

The samples were clamped in a solid sample holder in the right-angle mode. To prevent reflections of the excitation light, the samples were rotated by 30° relative to the excitation beam, with the result that only diffusely scattered emission light was detected. All samples were measured using identical spectrometer settings (gap widths 1 nm (excitation monochromator) and 1.5 nm (emission monochromator), scan range 372 to 700 nm, increment 1 nm, integration time 1 s, excitation wavelength 366 nm).

FIG. 1 shows, for the glass ceramic sample obtained according to Example 11, the emission spectrum at an excitation wavelength of 366 nm as well as excitation spectra for emission at 430 nm and 541 nm. The emission spectrum displayed a broad maximum at 430 nm, which is to be assigned to the 5d→4f transition of $Ce^{3+}$. The corresponding excitation spectrum displayed excitation maxima at 279 nm and 340 nm. Furthermore, the emission spectrum displayed maxima at 483, 541, 585 and 619 nm, which are to be assigned to the transitions $^5D_4 \rightarrow {}^7F_6$, $^7F_5$, $^7F_4$ and $^7F_3$ of $Tb^{3+}$. The associated broad excitation spectrum for emission at 541 nm displayed excitation maxima at 279 nm and 315 nm. The fluorescence emissions shown in the emission spectrum of FIG. 1 are perceived by the human eye overall as white-blue fluorescence.

Figure 2:
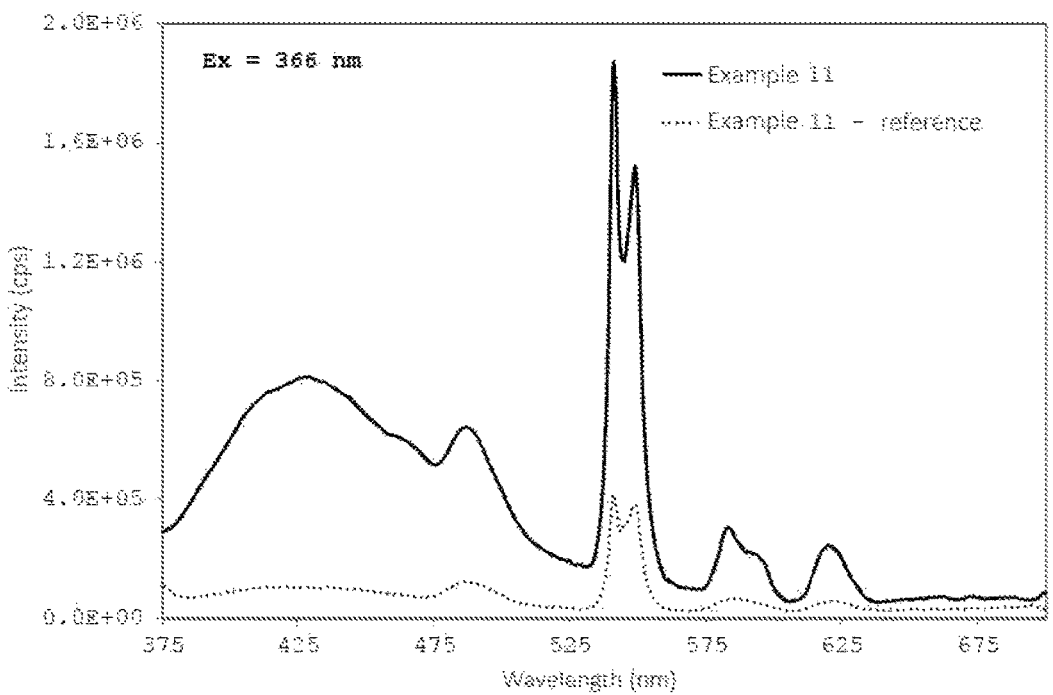

FIG. 2 shows emission spectra obtained at an excitation wavelength of 366 nm for the sample according to Example 11, which was prepared under reducing conditions by means of passing forming gas through it, and the corresponding reference sample of the same composition which was melted under normal conditions in oxygen-containing atmosphere. The broad emission maximum of $Ce^{3+}$ at about 430 nm and the emission bands of $Tb^{3+}$ at 483, 541, 549, 585 and 619 nm can be seen. A comparison of the spectra shows a clear rise in the intensities of the individual emission bands due to the melting under reducing conditions for the sample according to Example 11. A comparison of the total light emission, determined by calculation of the surface integral under the emission curves over the range of from 375 to 700 nm (total measurement range), shows a rise by a factor of 5.4.

FIG. 3 shows the emission intensities of the samples 1, 14, 8 and 9 compared with the commercial lithium disilicate glass ceramic products IPS e.max CAD HT BL2 and IPS e.max CAD LT A2 (Ivoclar Vivadent AG). The respectively used melting technology (forming gas, reducing raw material) makes it possible to greatly increase the fluorescence intensity compared with the commercial products. Thus, Example 1 showed a very strong fluorescence, which is why the composition is suitable in particular for use as abutment. Examples 9 and 14 are suitable in particular for use as inlay and crown material because of their colour (under normal illumination) and fluorescence (under UV light). By combining different cerium raw materials ($CeO_2$, Ce(III) acac), such as in the case of Example 9, it is possible to produce an intensive colour effect under D65 normal light and, compared with a commercial product of the same colour (IPS e.max CAD LT A2), a greatly increased fluorescence.

TABLE I

| Composition | 1 wt.-% | 2 wt.-% | 3 wt.-% | 4 wt.-% | 5 wt.-% | 6 wt.-% | 7 wt.-% | 8 wt.-% | 9 wt.-% | 10 wt.-% | 11 wt.-% | 12 wt.-% | 13 wt.-% | 14 wt.-% | 15 wt.-% |
|---|---|---|---|---|---|---|---|---|---|---|---|---|---|---|---|
| $SiO_2$ | 69.1 | 68.0 | 68.0 | 59.0 | 69.9 | 71.9 | 70.6 | 70.7 | 71.2 | 71.1 | 72.7 | 71.3 | 67.8 | 65.0 | 72.7 |
| $GeO_2$ | — | — | — | 2.9 | — | — | — | — | — | — | — | — | — | — | — |
| $ZrO_2$ | — | — | 6.0 | 6.0 | — | — | — | — | — | — | — | 2.0 | 6.0 | 9.8 | — |
| $Li_2O$ | 14.4 | 14.1 | 14.1 | 19.0 | 14.9 | 15.0 | 14.6 | 14.7 | 14.8 | 14.8 | 15.1 | 14.8 | 14.1 | 13.5 | 15.1 |
| $P_2O_5$ | 3.4 | 3.4 | 3.4 | 3.5 | 4.0 | 4.0 | 3.2 | 3.2 | 3.4 | 3.4 | 3.3 | 3.2 | 3.0 | 2.9 | 3.3 |
| $Al_2O_3$ | 3.4 | 3.3 | 3.0 | 3.0 | 3.0 | 3.0 | 3.4 | 3.4 | 3.4 | 3.4 | 3.5 | 3.4 | 3.2 | 3.1 | 3.5 |
| $K_2O$ | — | — | 3.5 | 4.0 | 3.5 | 3.5 | 3.8 | 3.8 | 3.9 | 3.9 | 3.2 | 3.1 | 3.7 | 3.5 | 3.2 |
| $Rb_2O$ | 7.7 | — | — | — | — | — | — | — | — | — | — | — | — | — | — |
| $Cs_2O$ | — | 9.2 | — | — | — | — | — | — | — | — | — | — | — | — | — |
| CaO | — | — | — | — | 2.0 | — | — | — | — | — | — | — | — | — | — |
| $CeO_2$ | — | — | — | — | — | — | 1.5 | 2.2 | 1.5 | 1.5 | 1.5 | 1.5 | 1.5 | 1.5 | 1.5 |
| $Ce_2O_3$* | 1.5 | 2.0 | 2.0 | 2.0 | 1.8 | 1.8 | 2.9 | 1.8 | 1.5 | 1.5 | — | — | — | — | — |
| $Tb_4O_7$ | 0.5 | — | — | 0.5 | 0.4 | 0.4 | — | — | — | — | — | 0.7 | 0.7 | 0.7 | — |
| $Tb_2O_3$ | — | — | — | — | — | — | — | — | 0.1 | 0.2 | — | — | — | — | — |
| $Gd_2O_3$ | — | — | — | — | — | 0.4 | — | — | — | — | — | — | — | — | — |
| $Er_2O_3$ | — | — | — | 0.1 | — | — | — | 0.1 | 0.1 | 0.1 | — | — | — | — | — |
| $Eu_2O_3$ | — | — | — | — | — | — | — | — | — | — | — | — | — | — | 0.7 |
| $V_2O_5$ | — | — | — | — | — | — | — | 0.1 | 0.1 | 0.1 | — | — | — | — | — |
| F | — | — | — | — | 0.5 | — | — | — | — | — | — | — | — | — | — |
| Σ | 100.0 | 100 | 100 | 100 | 100.0 | 100 | 100 | 100 | 100 | 100 | 100 | 100 | 100 | 100 | 100 |

*used as cerium(III) acetylacetonate

TABLE II

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| $T_N$ [° C.] | 520 | 560 | 530 | 500 | 500 | 510 | 470 | 490 | 490 | 490 | 500 | 500 | 500 | 500 | 500 |
| $t_N$ [min] | 30 | 60 | 20 | 40 | 90 | 80 | 10 | 10 | 10 | 10 | 10 | 10 | 10 | 10 | 10 |
| $T_{K1}$ [° C.] | 700 | 700 | 700 | 700 | 700 | 700 | 700 | 700 | 700 | 700 | 700 | 700 | 650 | 650 | 700 |
| $t_{K1}$ [min] | 20 | 20 | 20 | 20 | 20 | 20 | 20 | 20 | 20 | 40 | 20 | 20 | 20 | 20 | 20 |
| $T_{K2}$ [° C.] | 850 | 850 | 850 | 850 | 850 | 860 | 840 | 830 | 830 | 830 | 850 | 850 | 840 | 840 | 850 |
| $t_{K2}$ [min] | 7 | 7 | 7 | 7 | 7 | 7 | 7 | 7 | 10 | 7 | 10 | 10 | 7 | 7 | 10 |
| $\sigma_B$ [MPa] | 541.4 | | | | | | | | | | | | | | |
| L* | 93.37 | | | | | | | 79.04 | 84.02 | 81.95 | | | 89.08 | 86.05 | |
| a* | 0.06 | | | | | | | 5.61 | 2.54 | 3.4 | | | 0.14 | 1.29 | |
| b* | 4.37 | | | | | | | 25.03 | 18.93 | 19.69 | | | 12.22 | 10.68 | |
| CR | 93.37 | | | | | | | 78.38 | 79.89 | 83.2 | | | 52.59 | 70.75 | |

The invention claimed is:

1. Method for the preparation of a lithium silicate glass, a lithium silicate glass with nuclei which are suitable for forming lithium metasilicate and/or lithium disilicate crystals, or a lithium silicate glass ceramic, which comprises a step in which a melt of a starting glass is formed from a glass-forming composition which comprises $SiO_2$, $Li_2O$, nucleating agent, a cerium compound and at least one reducing agent.

2. Method according to claim 1, in which the at least one reducing agent is a compound which comprises at least one oxidizable carbon atom.

3. Method according to claim 2, in which the at least one reducing agent is an acetylacetonate.

4. Method according to claim 1, in which the starting glass comprises up to 5.0 wt.-% alkaline earth metal oxide.

5. Method according to claim 1, in which the starting glass comprises at least one of the following components:

| Component | wt.-% |
|---|---|
| $SiO_2$ | 55.0 to 75.0 |
| $Li_2O$ | 9.0 to 21.0 |
| $M_2O$ | 1.0 to 12.0 |
| $Al_2O_3$ | 0.5 to 5.0 |
| $P_2O_5$ | 0.5 to 12.0, | wherein $M_2O$ is selected from the group consisting of $Na_2O$, $K_2O$, $Rb_2O$ and $Cs_2O$.

6. Method according to claim 1, in which the starting glass furthermore comprises terbium ions.

7. Method according to claim 1 for the preparation of a lithium silicate glass with nuclei which are suitable for forming lithium metasilicate and/or lithium disilicate crystals.

8. Method according to claim 1 for the preparation of a lithium silicate glass ceramic which comprises lithium metasilicate as main crystal phase and/or comprises more than 10 vol.-% lithium metasilicate crystals.

9. Method according to claim 1 for the preparation of a lithium silicate glass ceramic which comprises lithium disilicate as main crystal phase and/or comprises more than 10 vol.-% lithium disilicate crystals.

10. Method according to claim 1, in which the starting glass is subjected to at least one heat treatment in the range of from 450 to 950° C. in order to form a lithium silicate glass with nuclei which are suitable for forming lithium metasilicate and/or lithium disilicate crystals, or a lithium silicate glass ceramic.

11. Method according to claim 1, in which the lithium silicate glass, the lithium silicate glass with nuclei suitable for forming lithium metasilicate and/or lithium disilicate crystals or the lithium silicate glass ceramic is present in the form of a powder, a blank or a dental restoration.

12. Method according to claim 1, wherein the lithium silicate glass, the lithium silicate glass with nuclei suitable for forming lithium metasilicate and/or lithium disilicate crystals and the lithium silicate glass ceramic have a fluorescence intensity at 430 nm which is at least 1.5 times the corresponding fluorescence intensity of a reference sample,
wherein the reference sample is obtainable by melting a starting glass with the composition: 71.3 wt.-% $SiO_2$, 15.1 wt.-% $Li_2O$, 3.2 wt.-% $K_2O$, 3.5 wt.-% $Al_2O_3$, 3.3 wt.-% $P_2O_5$, 1.5 wt.-% $CeO_2$ and 0.7 wt.-% $Tb_4O_7$ on a scale of 200 g from suitable raw materials in a platinum-rhodium crucible at 1500° C. for 1 h, pouring 30 g of the glass melt into a pre-heated mould to produce a glass block, and converting the glass block into a glass ceramic by successive temperature treatments at 500° C. for 10 min, 700° C. for 20 min and 850° C. for 10 min, wherein the heating rates between the temperature treatments are 30 K/min in each case.

13. Method according to claim 1, wherein the lithium silicate glass, the lithium silicate glass with nuclei suitable for forming lithium metasilicate and/or lithium disilicate crystals and the lithium silicate glass ceramic have a fluorescence intensity at 541 nm which is at least 1.5 times the corresponding fluorescence intensity of a reference sample,
wherein the reference sample is obtainable as defined in claim 12.

14. Method according to claim 1, which further comprises using the lithium silicate glass, the lithium silicate glass with nuclei suitable for forming lithium metasilicate and/or lithium disilicate crystals or the lithium silicate glass ceramic as dental material.

15. Method according to claim 3, in which the acetylacetonate comprises cerium acetylacetonate or cerium(III) acetylacetonate.

16. Method according to claim 5, in which the starting glass comprises the following components:

| Component | wt.-% |
|---|---|
| $SiO_2$ | 59.0 to 73.0 |
| $Li_2O$ | 13.0 to 19.0 |
| $M_2O$ | 2.0 to 5.0 |
| $Al_2O_3$ | 2.5 to 3.5 |
| $P_2O_5$ | 2.5 to 7.0. |

17. Method according to claim 8 wherein the lithium metasilicate glass ceramic comprises more than 20 vol.-% lithium metasilicate crystals.

18. Method according to claim 9 wherein the lithium silicate glass ceramic comprises more than 20 vol.-% lithium disilicate crystals.

19. Method according to claim 2, in which the at least one reducing agent is selected from the group consisting of organic salts, carbohydrates and cereal flours.

20. Method according to claim 4, wherein the alkaline earth metal oxide is CaO, BaO, MgO, SrO or a mixture thereof.

21. Method according to claim 1, which further comprises using the lithium silicate glass, the lithium silicate glass with nuclei suitable for forming lithium metasilicate and/or lithium disilicate crystals or the lithium silicate glass ceramic for the preparation of dental restorations.

22. Method according to claim 21, in which the lithium silicate glass, the lithium silicate glass with nuclei suitable for forming lithium metasilicate and/or lithium disilicate crystals or the lithium silicate glass ceramic is shaped by pressing or machining to form the desired dental restoration.

23. Method according to claim 22, wherein the desired dental restoration is an inlay, onlay, veneer, partial crown, crown or facet.

24. Glass-forming composition which comprises $SiO_2$, $Li_2O$, nucleating agent, a cerium compound and at least one reducing agent.

25. Glass-forming composition according to claim 24, which comprises as cerium compound and reducing agent a cerium compound which comprises at least one oxidizable carbon atom.

\* \* \* \* \*